US00PP32412P2

(12) United States Plant Patent
Heuger

(10) Patent No.: US PP32,412 P2
(45) Date of Patent: Oct. 27, 2020

(54) ***HELLEBORUS* PLANT NAMED 'COSEH 5200'**

(50) Latin Name: ***Helleborus* x *ericsmithii* X *Helleborus* x *hybridus***
Varietal Denomination: COSEH 5200

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 16/602,786

(22) Filed: Nov. 29, 2019

(51) Int. Cl.
*A01H 5/02* (2018.01)
*A01H 6/72* (2018.01)

(52) U.S. Cl.
USPC ..... Plt./439

(58) Field of Classification Search
USPC ..... Plt./263.1, 439
See application file for complete search history.

*Primary Examiner* — Susan McCormick Ewoldt
*Assistant Examiner* — Karen M Redden
(74) *Attorney, Agent, or Firm* — C. A. Whealy

(57) ABSTRACT

A new and distinct cultivar of *Helleborus* plant named 'COSEH 5200', characterized by its upright and mounded plant habit; moderately vigorous growth habit; dark green-colored leaves; moderately freely flowering habit; single purple-colored flowers; and good garden performance.

2 Drawing Sheets

Figure 1:
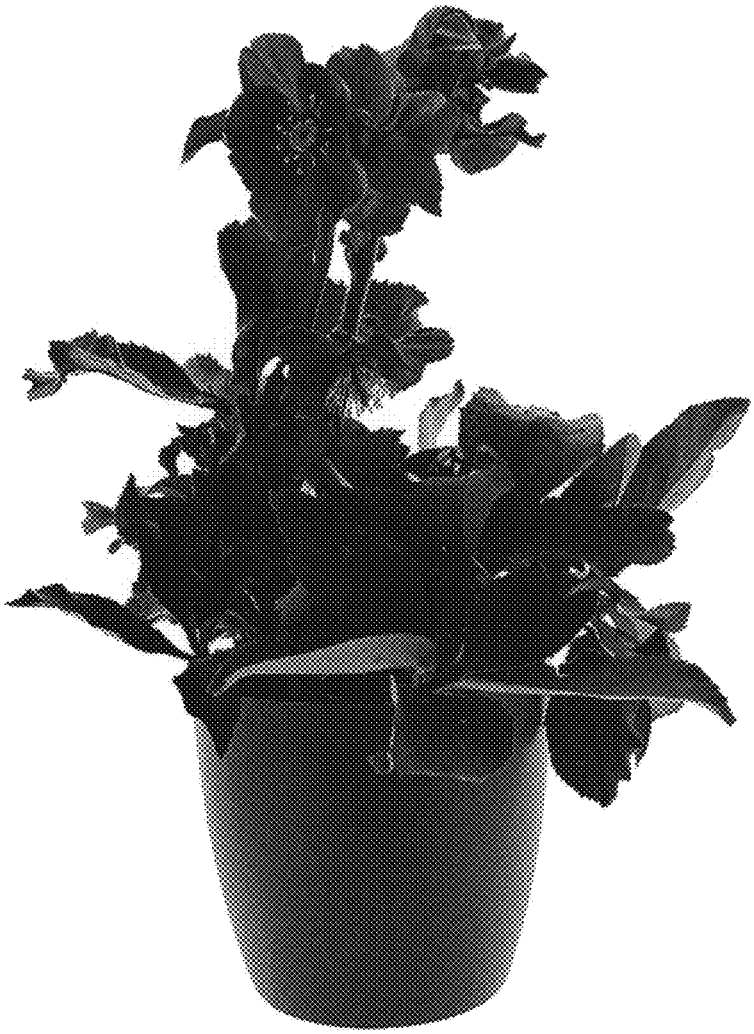

Botanical designation: *Helleborus* x *ericsmithii* X *Helleborus* x *hybridus*.
Cultivar denomination: 'COSEH 5200'.

CROSS-REFERENCED TO CLOSELY-RELATED APPLICATIONS

Title: *Helleborus* Plant Named 'COSEH 5100'
Applicant: Josef Heuger
Filed: Concurrently with the instant application U.S. Plant patent application Ser. No. 16/602,772
Title: *Helleborus* Plant Named 'COSEH 5300'
Applicant: Josef Heuger
Filed: Concurrently with the instant application U.S. Plant patent application Ser. No 16/602,773
Title: *Helleborus* Plant Named 'COSEH 5400'
Applicant: Josef Heuger
Filed: Concurrently with the instant application U.S. Plant patent application Ser. No. 16/602,792

BACKGROUND OF THE INVENTION

The present invention relates to a new and distinct cultivar of *Helleborus* plant, botanically known as *Helleborus* x *ericsmithii* X *Helleborus* x *hybridus* and hereinafter referred to by the name 'COSEH 5200'.

The new *Helleborus* plant is a product of a planned breeding program conducted by the Inventor in Glandorf, Germany. The objective of the breeding program was to create new uniform *Helleborus* plants with unique and attractive plant habit, leaf and flower coloration and tolerance to biotic and abiotic stress.

The new *Helleborus* plant originated from a cross-pollination conducted by the Inventor in Glandorf, Germany in December, 2012 of a unnamed selection of *Helleborus* x *ericsmithii*, not patented, as the female, or seed patent and an unnamed selection of *Helleborus* x *hybridus*, not patented, as the male, or pollen parent. The new *Helleborus* plant was discovered and selected by the Inventor as a single flowering plant from within the progeny of the stated cross-pollination grown in a controlled greenhouse environment in Glandorf, Germany in January, 2014.

Asexual reproduction of the new *Helleborus* plant by divisions in a controlled environment in Glandorf, Germany since April, 2014 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'COSEH 5200'. These characteristics in combination distinguish 'COSEH 5200' as a new and distinct *Helleborus* plant:

1. Upright and mounded plant habit.
2. Moderately vigorous growth habit.
3. Dark green-colored leaves.
4. Moderately freely flowering habit.
5. Single purple-colored flowers.
6. Good garden performance.

Plants of the new *Helleborus* differ from plants of the female parent selection in the following characteristics:

1. Plants of the new *Helleborus* are taller than plants of the female parent selection.
2. Plants of the new *Helleborus* have purple-colored flowers whereas plants of the female parent selection have cream-colored flowers.

Plants of the new *Helleborus* differ from plants of the male parent selection in the following characteristics:

1. Plants of the new *Helleborus* have fewer leaves than plants of the male parent selection.
2. Plants of the new *Helleborus* have darker green-colored leaves than plants of the male parent selection.

Plants of the new *Helleborus* can be compared to plants of *Helleborus* x *ericsmithii* X *Helleborus* x *hybridus* 'COSEH 5100', disclosed in a U.S. Plant Patent application filed concurrently. Plants of the new *Helleborus* differ primarily from plants of 'COSEH 5100' in flower color as plants of the new *Helleborus* have purple-colored flowers whereas plants of 'COSEH 5100' have light yellow green and red purple to greyed purple bi-colored flowers.

Plants of the new *Helleborus* can be compared to plants of *Helleborus* x *ericsmithii* X *Helleborus* x *hybridus* 'COSEH 5300', disclosed in a U.S. Plant Patent application filed concurrently. Plants of the new *Helleborus* differ primarily from plants of 'COSEH 5300' in growth and flowering habit as plants of the new *Helleborus* are not as vigorous or as freely-flowering as plants of 'COSEH 5300'.

Plants of the new *Helleborus* can be compared to plants of *Helleborus* x *ericsmithii* X *Helleborus* x *hybridus* 'COSEH 5400', disclosed in a U.S. Plant Patent application filed concurrently. Plants of the new *Helleborus* differ primarily from plants of 'COSEH 5400' in flower color as plants of the new *Helleborus* have purple-colored flowers whereas plants of 'COSEH 5400' have white and red purple bi- colored flowers.

Plants of the new *Helleborus* can also be compared to plants of *Helleborus* x *hybridus* 'Anna's Red', not patented. In side-by-side comparisons, plants of the new *Helleborus* differ primarily from plants of 'Anna's Red' in the following characteristics:

1. Leaves of plants of the new *Helleborus* have less distinct venation than leaves of plants of 'Anna's Red'.
2. Plants of the new *Helleborus* flower earlier than plants of 'Anna's Red'.
3. Flowers of plants of the new *Helleborus* are purple-colored whereas flowers of plants of 'Anna's Red' are red in color.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet (FIG. 1 of 2) is a side perspective view of a typical flowering plant of 'COSEH 5200' grown in a container.

Figure 2:
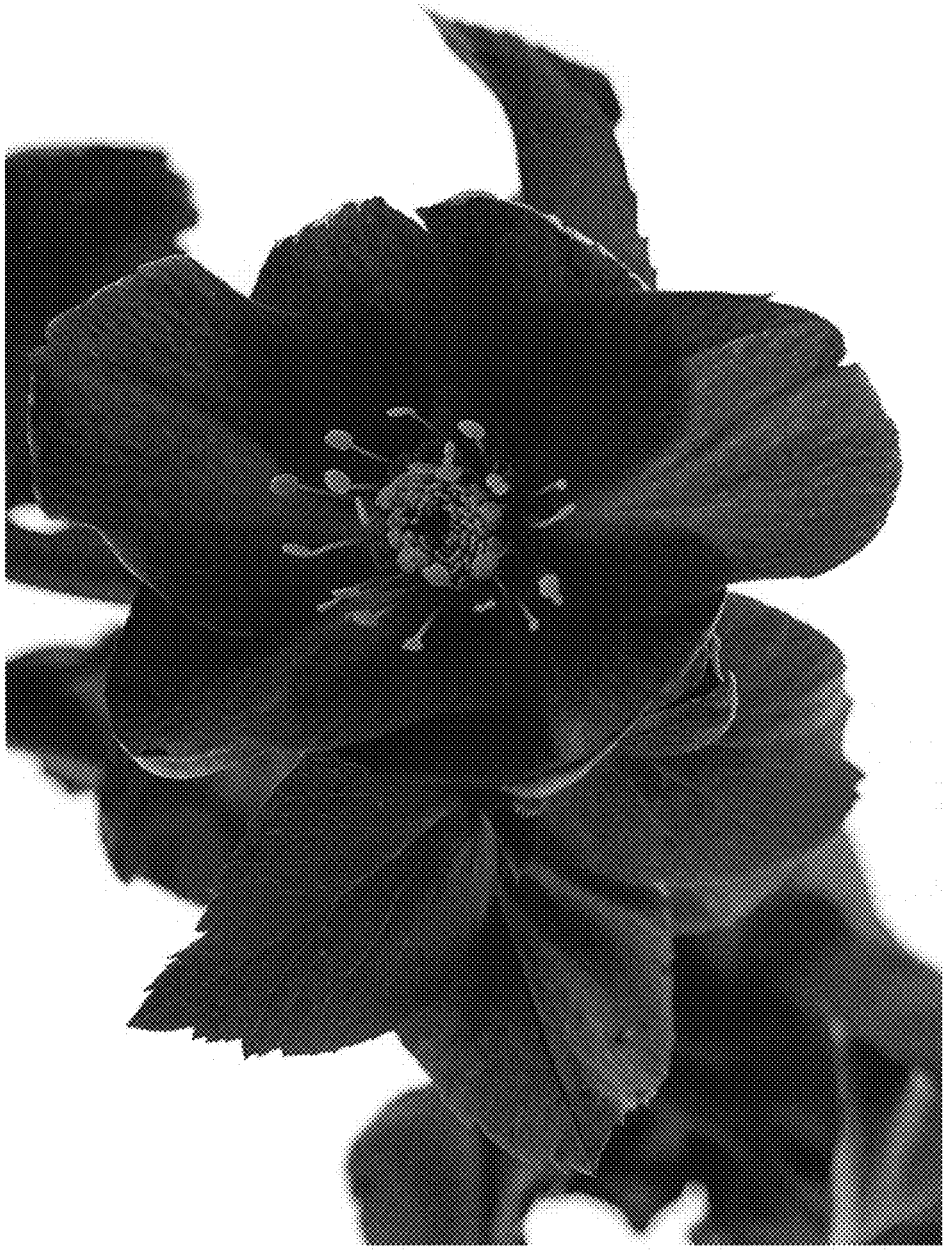

The photograph on the second sheet (FIG. 2 of 2) is a close-up view of a typical flower and leaves of 'COSEH 5200'.

DETAILED BOTANICAL DESCRIPTION

The aforementioned photographs and following observations, measurements and values describe plants grown during December in 17-cm containers in a glass-covered greenhouse in Glandorf, Germany and under cultural practices typical of commercial *Helleborus* production. During the production of the plants, day temperatures ranged from 12° C. to 32° C. and night temperatures ranged from 5° C. to 12° C. Plants were 14 months old when the photographs and the description were taken. In the following description, color references are made to The Royal Horticultural Society Colour Chart, 2015 Edition, except where general terms of ordinary dictionary significance are used.

Botanical classification: *Helleborus* x *ericsmithii* X *Helleborus* x *hybridus* 'COSEH 5200'.

Parentage:

*Female, or seed, parent*.—Unnamed selection of *Helleborus* x *ericsmithii*, not patented.

*Male, or pollen, parent*.—Unnamed selection of *Helleborus* x *hybridus*, not patented.

Propagation:

*Type*.—In vitro axillary meristem culture.

*Time to initiate roots, winter*.—About 55 days at temperatures about 12° C. to 32° C.

*Time to produce a rooted young plant, winter*.—About 170 days at temperatures ranging from 5° C. to 12° C.

*Root description*.—Thick to thin, fleshy; typically white to brown in color, actual color of the roots is dependent on substrate composition, water quality, fertilizer type and formulation, substrate temperature and physiological age of roots.

*Rooting habit*.—Low branching; sparse.

Plant description:

*Plant and growth habit*.—Herbaceous perennial; upright and mounding plant habit with flowers held within and above the foliar plane; plant shape, roughly flattened globular; moderately vigorous growth habit and moderate to rapid growth rate.

*Plant height, soil level to top of foliar plane*.—About 25.7 cm.

*Plant height, soil level to top of flowers*.—About 36 cm.

*Plant diameter* (*area of spread*).—About 34.7 cm.

Leaf description:

*Arrangement*.—Leaves arranged in a basal rosette; leaves palmately compound with typically five leaflets per leaf.

*Leaf length*.—About 16.8 cm.

*Leaf width*.—About 20.7 cm.

*Leaflet length*.—About 11.6 cm.

*Leaflet width*.—About 6.1 cm.

*Leaf shape*.—Palmate; reniform in outline.

*Leaflet shape*.—Elliptic to obovate.

*Leaflet apex*.—Acute.

*Leaflet base*.—Attenuate.

*Leaflet margin*.—Serrate; moderately undulate.

*Leaflet texture and luster, upper and lower surfaces*.—Smooth, glabrous; leathery; slightly glossy.

*Leaflet venation pattern*.—Pinnate.

*Leaflet color*.—Developing leaflets, upper surface: Close to 137A to 137B; midvein, close to 187C. Developing leaflets, lower surface: Close to 148A strongly tinged with close to N186C; midvein, close to 187A. Fully developed leaflets, upper surface: Close to darker than between 139A and N189A; venation, close to 147B. Fully developed leaflets, lower surface: Close to 137C; venation, close to 152A, proximally, close to N199A and N199B.

*Petioles*.—Length: About 12 cm. Diameter: About 4.5 mm to 6 mm. Strength: Strong. Texture and luster, upper and lower surfaces: Smooth, glabrous; slightly glossy. Color, upper and lower surfaces: Close to 144A to 144B; densely covered with fine dots and marbled with close to 183A.

Flower description:

*Flower shape and habit*.—Single rotate flowers; flowers slightly cupped; arranged solitary or in clusters with about three flowers each; moderately freely flowering habit with about 15 flowers developing per plant; flowers facing outwardly to slightly nodding.

*Fragrance*.—None detected.

*Natural flowering season*.—Plants begin flowering about ten months after planting; plants flower during the late autumn into the winter in Germany.

*Flower longevity on the plant*.—About three to four months; sepals persistent, other flower parts are not persistent.

*Flower buds*.—Length: About 2.8 cm. Diameter: About 1.5 cm. Shape: Oblong to ovate. Texture and luster: Smooth, glabrous; matte. Color: Close to N77B tinged with close to 148B.

*Inflorescence height*.—About 36.8 cm.

*Inflorescence diameter*.—About 15.3 cm.

*Flower diameter*.—About 9.2 cm by 9.2 cm.

*Flower depth* (*height*).—About 3 cm.

*Petals*.—All petals are transformed into nectaries.

*Sepals*.—Quantity and arrangement: About five, arranged in a single whorl. Length: About 4.4 cm. Width: About 4.7 cm. Shape: Reniform to broadly ovate, slightly to moderately concave. Apex: Obtuse. Base: Truncate to rounded. Margin: Entire; moderately undulate. Texture and luster, upper surface: Smooth, glabrous; matte. Texture and luster, lower surface: Smooth, glabrous; slightly glossy. Color: When opening, upper surface: Close to 64A. When opening, lower surface: Close to 63C and towards the margins and apex, close to 64A; venation, close to 61A. Fully opened, upper surface: Close to N77B; with development, close to 183A strongly tinged with close to N199A, towards the margins, slightly darker than between N77B and 186A. Fully opened, lower surface: Close to N77B and towards the base to close to 186B; with development, close to 187A and towards the apex to close to N186C.

*Flower bracts*.—Quantity per flower: Typically two. Length: About 5.6 cm. Width: About 3.7 cm. Shape: Broadly ovate. Apex: Acute. Base: Truncate. Margin: Finely serrate; slightly undulate. Color, upper surface: Close to NN137A to NN137B; venation, close to N186C. Color, lower surface: Close to 148B; venation, close to N186C.

*Peduncles*.—Length: About 28.5 cm. Diameter: About 6.5 mm to 8 mm. Aspect: About 10° from vertical. Strength: Strong. Texture and luster: Smooth, glabrous; slightly glossy. Color: Close to 145B; heavily and finely dotted, close to 183C.

*Pedicels*.—Length: About 5.1 cm. Diameter: About 3 mm. Aspect: About 10° from peduncle axis. Strength: Moderately strong. Texture and luster: Smooth, glabrous; moderately glossy. Color: Close to 200A.

*Reproductive organs*.—Stamens: Quantity per flower: About 120. Filament length: About 2 cm. Filament color: Close to 75D, distally, close to NN155A. Anther shape: Double and broadly reniform; basifixed. Anther size: About 2 mm by 2 mm. Anther color: Close to 154C. Pollen amount: Moderate. Pollen color: Close to 4D. Pistils: Quantity per flower: About four, occasionally three or five. Pistil length: About 9 mm. Stigma diameter: About 0.3 mm. Stigma shape: Club-shaped. Stigma color: Close to 150D. Style length: About 8 mm. Style color: Close to 187B. Ovary color: Close to 177D; margins, close to 187C. Nectaries (transformed petals): Quantity per flower: About 17. Length: About 1.2 cm. Diameter: About 4 mm. Shape: Tubular, flattened. Texture and luster, inner and outer surfaces: Smooth, glabrous; slightly glossy. Color, immature, inner and outer surfaces: Close to 144B, distally, close to 145C. Color, mature, inner and outer surfaces: Close to 146C to 146D, distally, close to 12A and proximally, close to 152A; with development, close to 146C, distally, close to 13A and proximally, close to 152A.

*Seeds and fruits*.—To date, seed and fruit development have not been observed on plants of the new *Helleborus*.

Garden performance: Plants of the new *Helleborus* have been observed to have good garden performance and to tolerate rain, wind, high temperatures about 35° C. and to be suitable for USDA Hardiness Zones 5 through 9.

Pathogen & pest resistance: To date, plants of the new *Helleborus* have not been observed to be resistant to pathogens and pests common to *Helleborus* plants.

It is claimed:

1. A new and distinct *Helleborus* plant named 'COSEH 5200' as illustrated and described.

* * * * *